United States Patent [19]

McNeel

[11] Patent Number: 5,470,484
[45] Date of Patent: Nov. 28, 1995

[54] METHOD AND APPARATUS FOR CONTROLLING THE FEED OF WATER TREATMENT CHEMICALS USING A VOLTAMMETRIC SENSOR

[75] Inventor: Thomas E. McNeel, Memphis, Tenn.

[73] Assignee: Buckman Laboratories International, Inc., Memphis, Tenn.

[21] Appl. No.: 181,254

[22] Filed: Jan. 13, 1994

[51] Int. Cl.[6] .................................................. B01D 21/30
[52] U.S. Cl. ..................... 210/746; 210/96.1; 210/198.1; 204/153.1; 204/407; 324/439; 422/82.01; 436/150
[58] Field of Search ........................... 210/85, 96.1, 143, 210/198.1, 709, 746, 912; 422/82.01; 436/150; 324/439, 444; 204/153.1, 406, 407

[56] References Cited

U.S. PATENT DOCUMENTS

| | | | |
|---|---|---|---|
| 1,944,803 | 1/1934 | Ornstein | 324/439 |
| 3,399,133 | 8/1968 | Gerdes et al. | 210/198.1 |
| 3,883,414 | 5/1975 | Fujinaga et al. | |
| 4,059,406 | 11/1977 | Fleet. | |
| 4,830,757 | 5/1989 | Lynch et al. | |
| 4,855,061 | 8/1989 | Martin | 210/709 |
| 4,923,599 | 5/1990 | Bowers | 210/96.1 |
| 4,928,065 | 5/1990 | Lane et al. | 324/439 |
| 5,186,798 | 2/1993 | Sakai et al. | 204/153.1 |

FOREIGN PATENT DOCUMENTS

| | | |
|---|---|---|
| 0417571A1 | 3/1991 | European Pat. Off. . |
| 0466303A2 | 1/1992 | European Pat. Off. . |
| 573745 | 9/1977 | U.S.S.R. ............... 210/96.1 |
| WO88/08532 | 11/1988 | WIPO . |

OTHER PUBLICATIONS

EPO Search Report dated Jun. 8, 1995 for International Application No. PCT/US95/00487.
H. Willard et al., "Instrumental Methods of Analysis", pp. 691–735, 1981.
G. H. Jeffery et al., "Textbook of Quantitative Chemical Analysis", pp. 519–642, 1989.

*Primary Examiner*—Joseph W. Drodge
*Attorney, Agent, or Firm*—Finnegan, Henderson, Farabow, Garrett & Dunner

[57] ABSTRACT

A method for controlling the chemical treatment of a solution comprises the steps of feeding a treatment chemical into the solution, applying an external voltage across a reference electrode and a working electrode of a voltammetric sensor while the electrodes are immersed in the solution, measuring a current that flows through the working electrode, converting the measured current into a feedback signal indicative of the concentration of treatment chemical in the solution, and using the feedback signal to control the rate of feeding the treatment chemical.

20 Claims, 6 Drawing Sheets

METHOD AND APPARATUS FOR CONTROLLING THE FEED OF WATER TREATMENT CHEMICALS USING A VOLTAMMETRIC SENSOR

BACKGROUND OF THE INVENTION

1. Field of the Invention

The present invention relates to controlling the feed of water treatment chemicals. More particularly, the present invention relates to the use of a voltammetric current measurement as a feedback signal for a controller that provides on-off or proportioning control of the introduction of chemicals for the treatment of water and wastewater.

2. Description of the Related Art

A wide variety of chemicals are added to industrial process, boiler, and cooling water for use as microbicides, corrosion inhibitors, scale inhibitors, etc. Likewise, chemicals are added to wastewater for similar purposes or as purifying agents, such as heavy-metal precipitants, flocculants, etc.

There are several reasons why it is desirable to control the level of these compounds in a water system. Adding too much treatment chemical (overfeeding) is wasteful and can prevent the treatment program from being cost-effective. Overfeeding can cause unacceptably high levels of treatment chemicals to appear in the discharge water which, in turn, may present environmental impact problems and may interfere with the operation of biological waste treatment facilities. In this manner overfeeding can cause an industrial facility to be in violation of its wastewater discharge permits.

Further, feeding the treatment chemicals at too low a rate, i.e., underfeeding, will cause the treatment program to be ineffective. In the case of microbicide use, there may not be enough chemical present to control the growth of microorganisms. In the case of wastewater treatment using a precipitant for the so-called "heavy" metals, i.e., those transition metals which are toxic and will cause environmental harm if discharged into rivers, lakes, or other natural water sources, underfeeding the precipitant will allow toxic levels of the heavy metals to be discharged. In this manner underfeeding can also cause an industrial facility to be in violation of its wastewater discharge permits. Thus, failure to control levels of water treatment chemicals can have obvious harmful consequences for the environment.

Two techniques for controlling the feed of a water treatment chemical have been proposed. In the first control technique, the treatment chemical is added until a small excess is detected, and then addition of the chemical is stopped as soon as possible to minimize overfeeding. Ideally, there would be no excess treatment chemical used. This technique is very similar to a titration. An example of a situation in which this technique is used involves the precipitation of lead (Pb++) or copper (Cu++) from a wastewater stream using sodium dimethyldithiocarbamate. The exact quantity of treatment chemical that is required by the stoichiometry of the metal-dithiocarbamate reaction would be used, since a significant level of excess dimethyldithiocarbamate ion is not needed to ensure complete removal of these metals from the wastewater. Since it is unnecessary to know the actual level of excess treatment chemical in the water, the method used to detect the treatment chemical need not be very precise or accurate; and a wide linear range will not be essential. However, the response time must be very fast to minimize overfeeding; and the method must be sensitive enough to give a detectable response to a small level of excess treatment chemical.

In the second proposed control technique, the water treatment chemical is added until a specific concentration level of the chemical exists in the water, and additional chemical is added as needed to maintain this level. An example of a situation in which this technique would be used is the addition of a microbicide to whitewater in a paper machine. A certain level of the microbicide (often 100 ppm or less) will be needed to inhibit the growth of microorganisms, and it will be necessary to maintain this level within certain limits. If the microbicide level drops too low, the population of microorganisms may begin to grow to levels that interfere with the operation of the paper machine. On the other hand, if the microbicide level is too high, the excessive chemical usage will waste money; it may cause problems (such as discoloration) in the manufacture of paper; and the chemical may appear in the wastewater from the paper mill and thus may cause wastewater discharge problems. The method used to measure the level of treatment chemical in the water must be sufficiently precise to accurately determine if the level of treatment chemical is within the desired range. While response time and sensitivity are also important, these characteristics generally will not be as critical for this situation as for the titration-type control technique described above. Sensitivity only needs to be high enough to make an accurate determination of the compound at the selected use level. Once the required level of treatment chemical is established in the system, changes in the level will be relatively slow, and the rapid response needed to halt the addition of the treatment chemical in the treatment method described above will not be needed. The design of control equipment and techniques that can be used to carry out both of these control procedures is an important object of this patent.

Figure 1:
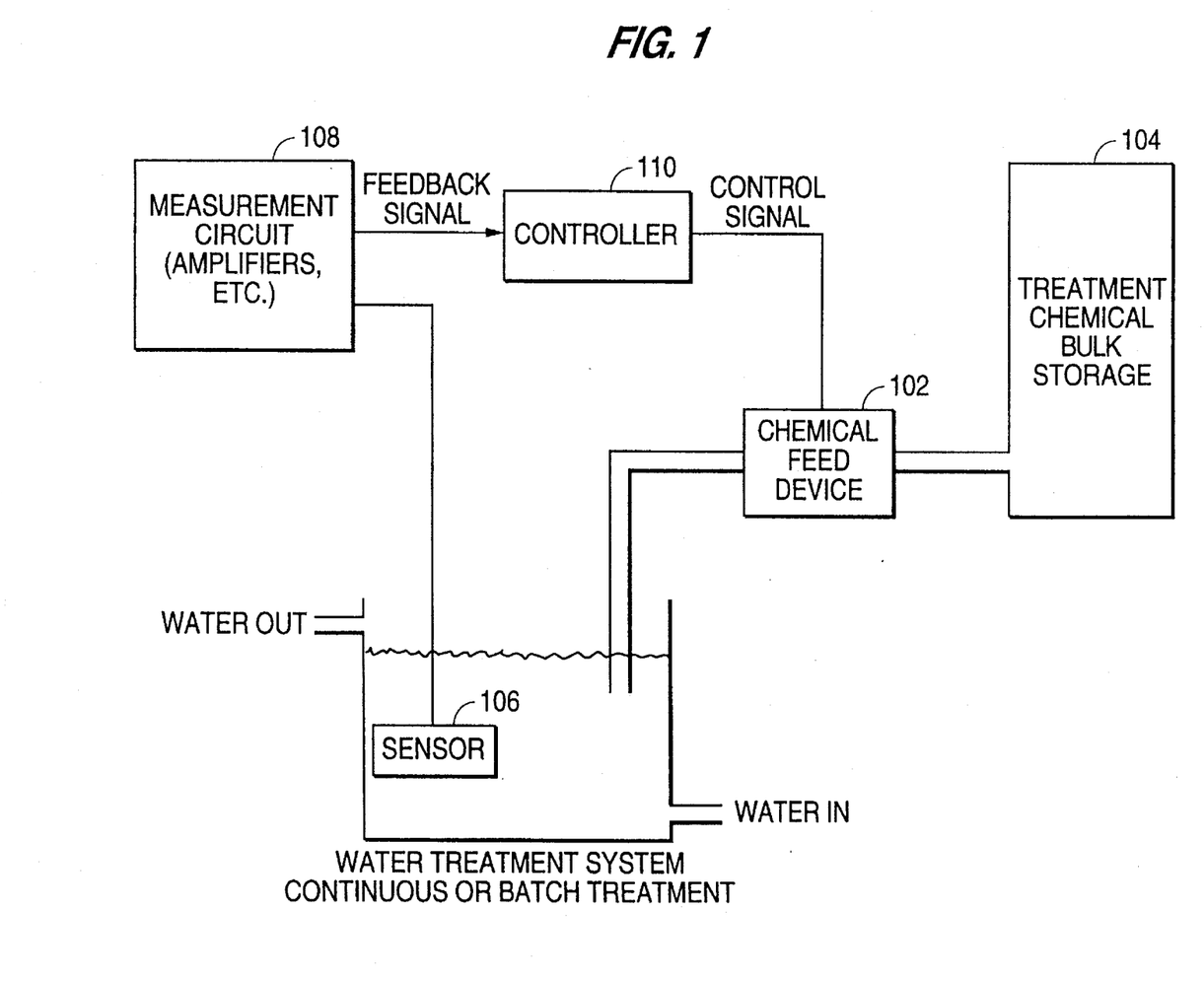
FIG. 1 is a block diagram of a chemical feed system.

As shown in FIG. 1, control of any water treatment process, such as precipitation of heavy metals from wastewater, requires three fundamental components:

1. A chemical feed device 102 for which the speed (feed rate) can be electrically controlled will be necessary. This feed device will usually be a pump for the introduction of liquid treatment chemicals from, for example, treatment chemical bulk storage 104, but a screw feeder equipped with a variable-speed motor may be used to introduce solid treatment chemicals.

2. A sensor 106 and associated electronics 108 will be needed to detect the amount of treatment chemical that is in the system or is needed by the system. This sensor 106 will produce a feedback signal that is sent to a controller.

3. A controller 110 will be needed (a) to compare the feedback signal from the sensor 106 with a signal that would correspond to the desired level of treatment chemical and (b) to make adjustments in the speed of the chemical feed device 102 so that the level of treatment chemical detected in the water corresponds to the desired level.

These three components must be present in some form to maintain control over the level of water treatment chemicals used. It is especially true that, in the absence of feedback, effective control cannot be achieved. In some cases, a person may perform the function of one or more of the components. For example, in the simplest configuration possible, a person may take a water sample, analyze it chemically (the function of the sensor), calculate and weigh out the amount of treatment chemical needed (the function of the controller) and manually add the treatment chemical (the function of the chemical feed device). However, for many operations it would be preferable to perform these functions automatically. Automated control is less expensive than manual control in many instances, and a properly designed automated system should be able to control the levels of treatment chemicals more precisely and more reliably than human operators. Automatic controllers that can be used for this purpose will implement ON/OFF or proportional/integral/derivative (PID) control algorithms and are available from a number of manufacturers, such as Honeywell, Inc. of Minneapolis, Minn. and Fenwal, Inc. of Ashland, Mass. It is a primary object of this patent to render automatic control possible through the use of voltammetric sensors to provide the required feedback signal.

There are two fundamental approaches that can be used to generate a feedback signal for the controller. In the first of these two approaches, the sensor 106 responds directly to the concentration of treatment chemical present in the water and generates a feedback signal directly proportional to the concentration of treatment chemical. In other words, the feedback signal increases as the level of treatment chemical increases. An example of such an application might involve the use of glutaraldehyde or a dithiocarbamate salt to control the growth of microorganisms in the water. An appropriate sensor 106 would respond directly to the level of the microbicide in the water.

In the second approach, the sensor 106 may respond to a substance in the water with which the treatment chemical is intended to react rather than the level of treatment chemical. In this manner the sensor 106 would generate a feedback signal that is inversely proportional to the level of treatment chemical. In other words, the feedback signal would decrease as the level of treatment chemical increases. An example of such an application might involve the use of sodium dimethyldithiocarbamate to precipitate certain specific heavy metals from a waste stream. In a system that contains a very limited variety of metals, it would be possible to provide a feedback signal for each metal using anodic stripping voltammetry. An on-line device for making this type of measurement is available from Ionics, Inc. of Watertown, Mass.

Some situations will require the use of feedback signals that are directly proportional to the level of treatment chemical in the system. One example of this case would be the maintenance of a given level of microbicide as described above. Another example would involve the use of a dimethyldithiocarbamate salt to precipitate a variety of metal ions from a waste stream. In this instance it would be unnecessary to determine the level of each of the metal ions in the wastewater in order to adjust the amount of dithiocarbamate added; it would only be necessary to establish and maintain a predetermined level of excess dithiocarbamate in the waste stream. If there is a sufficient level of excess dithiocarbamate in the wastewater, then it may be assumed that all of the dissolved "heavy" metals have been precipitated. The determination of the dithiocarbamate concentration would be far simpler than the determination of the levels of all the heavy metals in the wastewater.

On the other hand, certain situations will require the use of a feedback signal that is indirectly related to the level of treatment chemical in the system. For situations that involve the removal of a toxic substance from a waste stream, this technique is desirable since the feedback signal not only controls the feed of treatment chemical, but also provides a direct, recordable measurement of the level of the toxic substance in the waste stream. Records of these measurements can be used to document compliance or noncompliance with the wastewater discharge permit of the facility.

For example, the discharge permit of a wastewater treatment facility that uses sodium dimethyldithiocarbamate to precipitate heavy metals may have a limit on the level of dimethyldithiocarbamate ion that can be present in the final effluent water. A sensor 106 that responds directly to the level of excess dimethyldithiocarbamate ion in the waste stream can be used to generate a feedback signal to control the feed of a solution of ferrous ion, which reacts with and thus precipitates the excess dithiocarbamate ion. A recording of the level of dithiocarbamate ion detected, i.e., the feedback signal, will verify that the dithiocarbamate ion has been adequately removed from the waste stream. Unfortunately, not all toxic substances that must be removed from effluent wastewater can be determined conveniently by on-line analytical methods. It is another important object of this invention to provide a method for generating feedback signals that can be used for direct or indirect control of the feed of water treatment chemicals and for documenting compliance with the wastewater discharge permit.

To generate an effective feedback signal, the sensor 106 must perform a quantitative analysis of the process water or waste stream to control the level of treatment chemical desired. Many conventional laboratory techniques have been automated so that they may be used for on-line measurements. On-line equipment for colorimetric analyses is available from the Hach Co. of Loveland, Colo. Likewise, on-line equipment for turbidimetric analyses has been described in U.S. Pat. No. 4,923,599.

Electrochemical measurements are well suited as a basis for generating a feedback signal for several reasons:

(1) Many of the chemicals used in water and wastewater treatment may be determined using electrochemical techniques.

(2) The equipment needed for electrochemical measurements is inexpensive compared to the equipment needed for on-line colorimetric measurements or chromatographic (HPLC) measurements.

(3) Electrochemical sensors are fairly simple and are typically rugged and reliable. Unlike on-line colorimetric and turbidimetric measurements, which would require pumps to keep a portion of the process or waste stream flowing through the optical cells, electrochemical sensors do not have moving parts which have a high probability of failure.

(4) Electrochemical sensors are easier to maintain than colorimetric or turbidimetric which require time and labor intensive dismantling and cleaning. This feature is important because exposure to process or waste streams, especially those containing a high level of suspended solids, will rapidly contaminate the surface of any measurement device. If the electrochemical sensor is accessible, simple manual wiping may be sufficient for electrode maintenance. Inaccessible sensors require a different cleaning technique.

A proposed technique for making electrochemical measurements includes potentiometric methods, which involve the measurement of the voltage that develops on the surface of an electrode when it is immersed in a solution. The voltage is measured against a reference electrode, such as the silver/silver chloride (Ag/AgCl) couple or a saturated calomel electrode (SCE). Voltage measurement devices used for this technique must draw as little current through the electrodes as possible so that the electrode potentials will not be altered by the measurement. In other words, a very high-impedance measurement circuit must be used. In an ideal potentiometric measurement, no current should pass through the electrodes whatsoever. In practice, commonlyused voltage-measurement circuits are designed to draw less than one picoampere (1 pA or $10^{-12}$ ampere) through the electrodes. Maximum input currents in the low femtoampere (fA or $10^{-15}$ ampere) range can be achieved using currently-available electrometer amplifiers, such as the AD549L amplifier manufactured by Analog Devices, Inc. of Norwood, Mass.

However, using potentiometric measurements to generate a feedback signal in a control system have not provided satisfactory results. To begin with, the voltage that is measured in a potentiometric determination is directly proportional to the logarithm of the concentration of the substance that is being detected. This logarithmic relationship requires complicated electronic equipment to obtain a display of the measured concentration, e.g., %, ppm, etc. Hence, the logarithmic relationship obtained in potentiometric measurements lowers the accuracy and resolution of the concentration determination, and this limitation reduces the accuracy with which the concentration level can be controlled. In other words, the control system may not be able to detect and respond to changes in the concentration of the treatment chemical in the water unless those changes are large, i.e., changes by factors of 2–3 or more.

Further, the response time for potentiometric measurements can be very slow, especially for ion-selective electrodes used in solutions containing very low concentrations of analyte. This response time can be on the order of minutes, and a feedback signal with such a slow response time may not give the controller enough time to respond to a concentration change in the system, especially for a flow-through design. By the time such a sensor has responded to a sudden change in the demand for the treatment chemical, it could be too late for the control system to adjust the speed of the chemical feed device to maintain an adequate level of treatment chemical in the stream. During the time that the sensor is responding to the change in demand for treatment chemical, the wastewater that is discharged will be inadequately treated or will contain a large excess of treatment chemical. In either case, the discharge permit of the facility may be violated.

In addition, the performance of the extremely high-impedance measurement circuits required for potentiometric measurements can be severely degraded by the presence of moisture or chemical contamination, which are common in an industrial environment.

Finally, a mixed potential measurement, such as an oxidation-reduction (ORP) determination, is the net result of the influence of several factors, such as pH and the presence of oxidizing or reducing agents. There is no way to distinguish or resolve the different components that determine the measured potential.

SUMMARY OF THE INVENTION

Accordingly, the present invention is directed to a control system that substantially obviates one or more of the problems due to limitations and disadvantages of the related art.

To achieve these and other advantages and in accordance with the purpose of the invention, as embodied and broadly described, the invention involves applying an external voltage across a reference electrode and a working electrode in a solution to be treated, measuring a current that flows through the working electrode, converting the measured current to a voltage which is proportional to the amount of treatment chemical in the solution to be treated, and amplifying the converted voltage to produce a feedback signal.

In another aspect, the invention involves applying a desired external voltage, measured between a reference electrode and working electrode, across a counter electrode and working electrode in a solution to be treated, using the working electrode to measure a current that flows through the solution, converting the measured current into a voltage which is proportional to an amount of treatment chemical in the solution to be treated, and amplifying the converted voltage to produce a feedback signal.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate several embodiments of the invention and together with the description serve to explain the principles of the invention.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

DESCRIPTION OF THE INVENTION

In a system for controlling the feed of water treatment chemicals, feedback can be determined by taking electrochemical measurements using voltammetric techniques, which involve the application of a voltage across two electrodes in a solution and the measurement of the current that flows between the electrodes. The electrode at which the desired oxidation or reduction takes place is called the working electrode, and the applied potential (voltage) on the surface of this electrode is measured against the same type of reference electrode that is used to make potentiometric measurements. In the example involving the use of dimethyldithiocarbamate ions to precipitate metal ions from wastewater, dimethyldithiocarbamate ions are oxidized at the working electrode at an applied potential of +300 millivolts vs. Ag/AgCl. The working electrode measures an electric current flowing through the solution as a result of this oxidation reaction directly proportional to the level of dithiocarbamate ions in the water and thus may be amplified for use as a feedback signal to control the pump feeding dithiocarbamate ions into the system. Likewise, by adjusting the applied voltage, an electric current that is proportional to the concentration of an aldehyde, such as formaldehyde, glutaraldehyde, or a compound that is capable of releasing either of these compounds into the process or wastewater, may thus be measured. This current may be converted to a voltage and amplified for use as a feedback signal for controlling the pump that feeds the aldehyde to the system.

However, in some cases, the direct-current (DC) measurement equipment used in the voltammetric technique described above may provide an erratic signal, making it difficult to measure and establish a specific level of treatment chemical in the system. The erratic behavior of this measurement signal is due to motion of the sample solution past the surface of the working electrode. This motion may be due to temperature convection as well as mixing of the treated water by a mechanical agitator. The presence of a high level of suspended solids in the water to be treated, such as a clay slurry, adds an additional complication to both control techniques in that the suspended solids will prevent diffusion of the molecules of the treatment chemical to the electrode surface, which results in decay of the measurement signal with time.

Both of these problems can be alleviated using the technique of chronoamperometry, in which the applied voltage is a pulse train instead of a steady d.c. voltage. Between pulses, the applied voltage is held at a level at which there is little or no oxidation or reduction of the treatment chemical, and thus the measured cell current is negligibly small. However, during the pulses, the applied voltage is shifted to a level at which the treatment chemical is oxidized or reduced. The current that is measured during the application of the applied voltage pulse is initially very high and rapidly decays to a steady-state level. The component of the signal that decays with time is the sum of a non-faradaic charging current and a faradaic signal that is a function of the concentration of the treatment chemical that is being measured. At any given time after the application of the voltage pulse, the faradaic current signal will be directly proportional to the concentration of treatment chemical in the water. The non-faradaic charging current decays rapidly (within a matter of milliseconds for electrodes with exposed areas of no more than a few square millimeters), so it can be ignored by waiting a few milliseconds after the initial application of the pulse before the cell current is measured. The cell current should be measured at a specific time after the initial application of the voltage pulse, and the current signal that is measured at that time must be stored until it is updated during the next voltage pulse. Accurate timing circuits are needed to generate the voltage pulses and to control the sample-and-hold circuit that stores the cell current measurement between voltage pulses.

Figure 2:
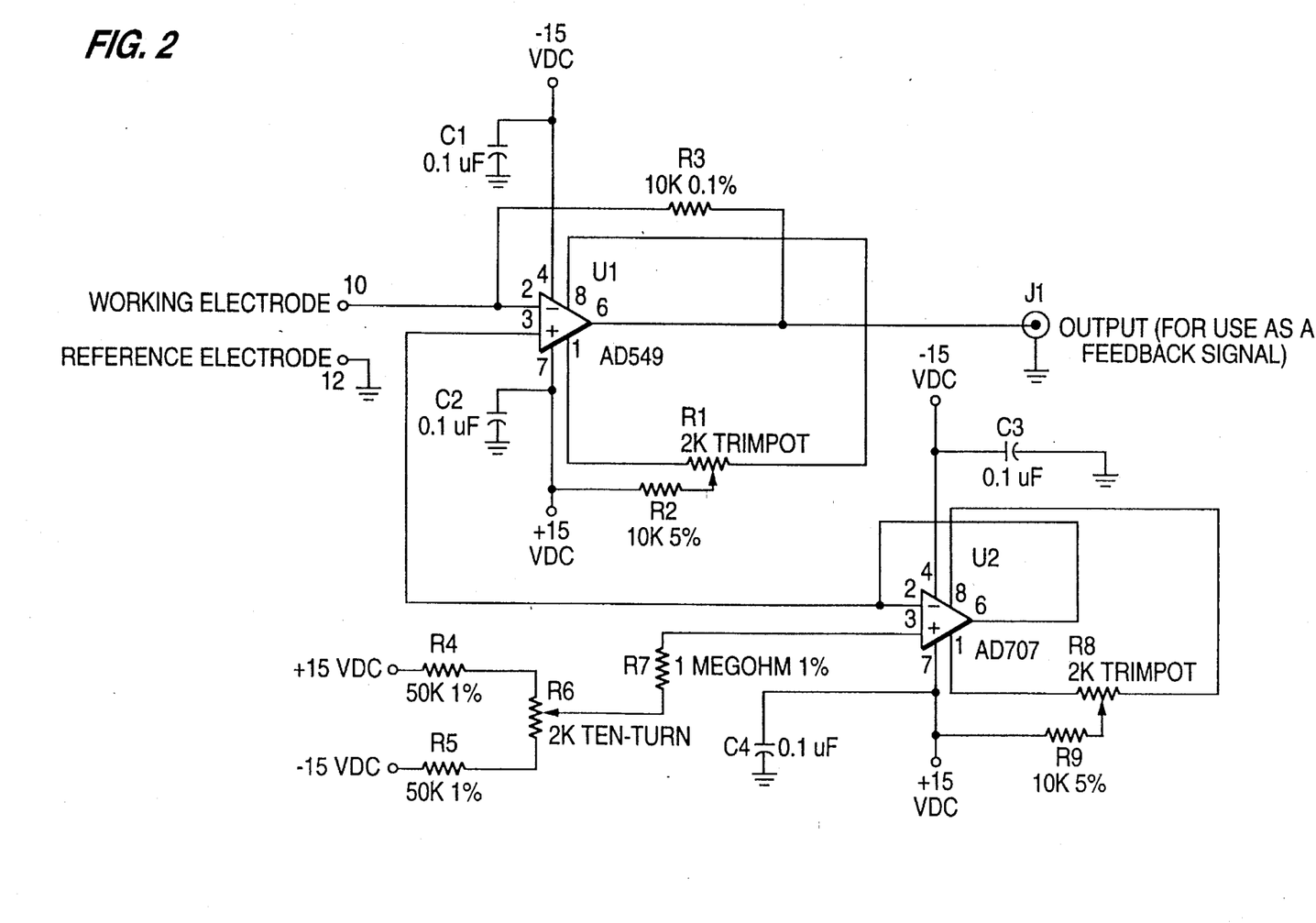
FIG. 2 is a circuit diagram of a two-electrode voltammetry system constructed in accordance with a first embodiment of the invention.

A preferred embodiment of a two-electrode circuit for producing a feedback signal in a control system is shown in FIG. 2. Operational amplifier U1, such as a Analog Devices AD549, is used as a current-to-voltage converter, for which negative feedback is provided through resistor R3. The voltage appearing at the output of amplifier U1 will be equal to R3 x the current measured by the working electrode connected to terminal 10. Since the measured current in small voltammetric cells can be on the order of nanoamperes or less, the use of an operational amplifier with low input current (preferably less than 1 picoampere) is required. The voltage that is applied to the working electrode is measured with respect to ground, terminal 12 to which the reference electrode is connected, and appears at pin 2 of amplifier U1. Since amplifier U1 is operating with negative feedback, the voltages at pins 2 and 3 (the inverting and noninverting inputs, respectively) will be equal to each other and will be determined by the output of voltage follower U2, such as an Analog Devices AD707. Resistors R4, R5, and R6 form a voltage divider which is used to select the input voltage and thus the output voltage of voltage follower U2. Resistor R7 limits the current flow into the noninverting input of voltage follower U2.

Trimpots R1 and R8 are used to null the input offset voltages for amplifier U1 and voltage follower U2, respectively. Resistors R2 and R9 limit current flow through the input offset adjustment circuits for amplifier U1 and voltage follower U2, respectively. Capacitors C1, C2, C3, and C4 are used to prevent power supply noise and oscillation.

The two-electrode circuit of FIG. 2 is a simple circuit that produces an effective feedback signal at terminal J1 for a control system.

As current passes through the reference electrode connected at terminal 12, an oxidation or reduction reaction may occur, altering the components of the reference electrode. Depending upon the electrode design, this alteration can change the potential of the reference electrode, against which the voltage applied to the working electrode is measured. Thus, the voltage that is applied to the working electrode will shift as current passes through the cell, and this shift in applied voltage can alter the measured cell current. In this manner an error can be introduced into the cell current measurement, in turn, introduces an error into the feedback signal.

Further, as current flows through the sample solution between the electrodes, a voltage drop will develop between the electrodes that is proportional to the cell current. Ohm's law indicates that this voltage drop will be equal to the resistance of the solution multiplied by the cell current. Obviously, this voltage drop will reduce the voltage that is applied to the working electrode, and the extent of this reduction will depend upon the magnitude of the cell current. As described above, the error in the applied voltage will be translated into an error in cell current, and, consequently, an error will appear in the feedback signal sent to the controller for the chemical feed device.

Figure 3:
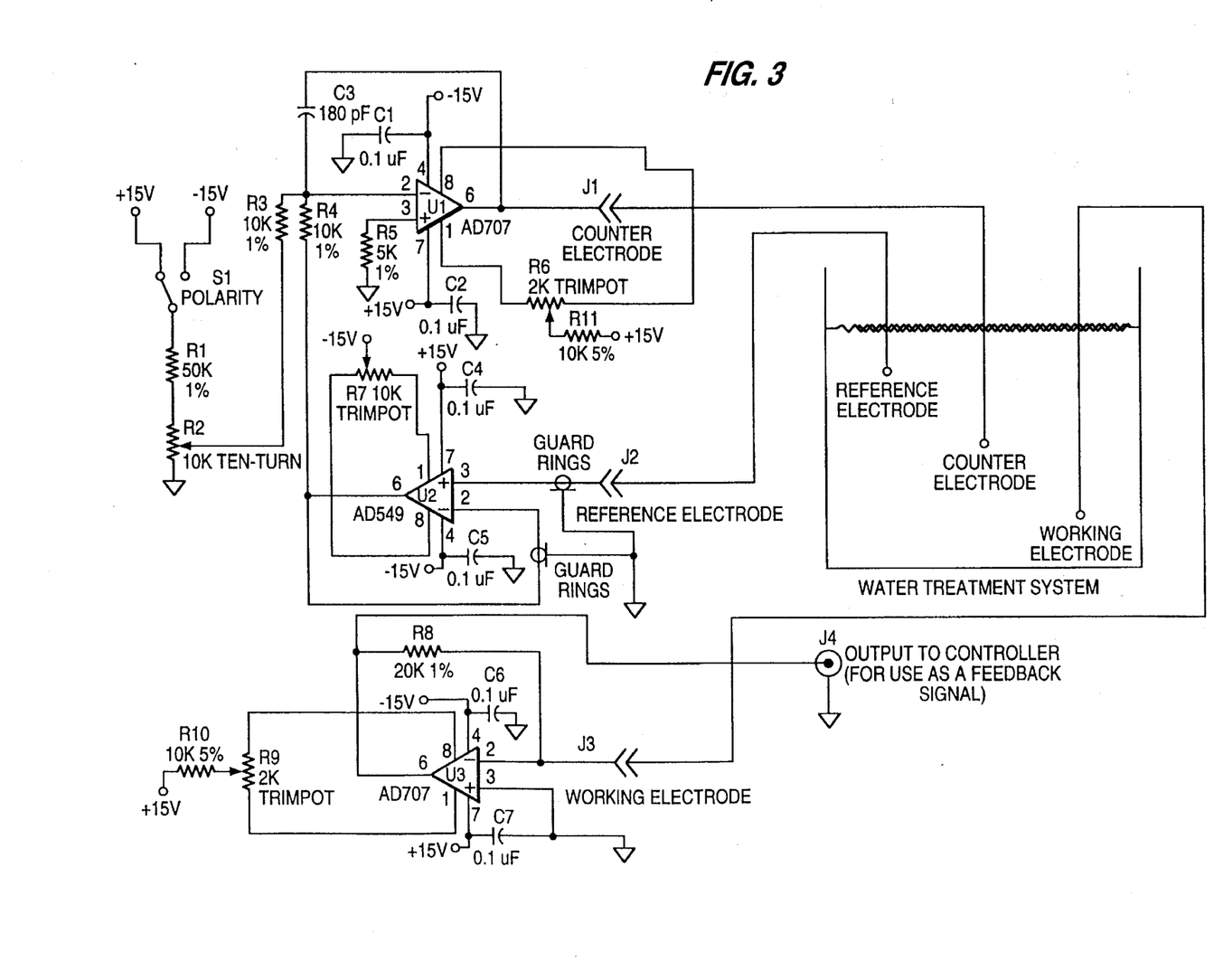
FIG. 3 is a circuit diagram of a DC potentiostat constructed in accordance with a second embodiment of the invention.

In a second embodiment, the three-electrode circuit shown in FIG. 3 is provided for producing a feedback signal in a control system. In this measurement circuit (also known as a potentiostat), an external voltage is applied between a counter electrode and a working electrode, which are shown in FIG. 3 immersed in the solution. This external voltage is automatically adjusted so that the potential at the surface of the working electrode, as measured against the reference electrode voltage, is equal to a desired value. The current that flows through the working electrode is measured and is referred to as the cell current. As described above, the cell current is directly proportional to the concentration of the substance that is being oxidized or reduced at the surface of the working electrode. The measurement of the potential at the surface of the working electrode is made using a high-impedance voltage-measuring circuit so that a current of one microampere ($10^{-6}$ ampere) or less is allowed to pass through the reference electrode. While it is not necessary to use the extremely high input impedance of the circuitry used in potentiometric measurements, the input impedance is still high enough to prevent significant changes in the composition of the reference electrode and to make the voltage drop across the solution negligible. These improvements in the accuracy with which the applied voltage is controlled will justify the increase in complexity of the measurement circuit.

The circuit shown in FIG. 3 compares the potential difference between the reference and working electrodes, buffered through the high-impedance voltage follower U2, with a desired applied voltage and adjusts the voltage that is applied to the counter electrode, connected at terminal J1, so that the desired applied voltage appears between the working electrode connected at terminal J3, and the reference electrode. The potential of the working electrode vs. the reference electrode is subtracted from the desired applied voltage by adding the desired applied voltage, supplied through resistor R3, to the potential of the reference electrode, which is measured with respect to the working electrode, maintained at ground potential, and is supplied through resistor R4. This difference signal at the inverting input of U1 is compared with the potential at the noninverting input, which is tied to ground through resistor R5, and the resulting error signal is amplified by the open-loop gain of U1 to supply the appropriate voltage to the counter electrode. The magnitude of the desired applied voltage is determined by the voltage divider R1 and R2, and the polarity is selected by switch S1. Capacitor C3 is needed to prevent oscillation of operational amplifier U1, since this amplifier is used without a feedback loop.

Trimpots R6, R7, and R9 are used to null the input offset voltages for amplifiers U1, U2, and U3, respectively. Resistors R10 and R11 limit current flow through the input offset adjustment circuits for amplifiers U3 and U1, respectively. Capacitors C1, C2, C4, C5, C6, and C7 are used to prevent power supply noise and oscillation.

Voltammetric measurements in water treatment or wastewater treatment systems may be made using the two-electrode or three-electrode techniques described above. The working and counter electrodes should be made from chemically-inert, electrically-conductive materials. The surface area of the counter electrode should be much larger than the working electrode so that the cell current will definitely be limited by the reaction at the working electrode rather than the reaction at the counter electrode. Platinum, gold, or some form of carbon, such as glassy carbon or pyrolytic graphite, are typically used. A nickel or graphite rod may be used as a counter electrode. Voltammetric determinations of organic compounds, such as dithiocarbamate salts, that contain sulfur in a reduced form should be made using a carbon electrode as the working electrode, since these compounds often react with and coat the surface of metallic electrodes.

Figure 4:
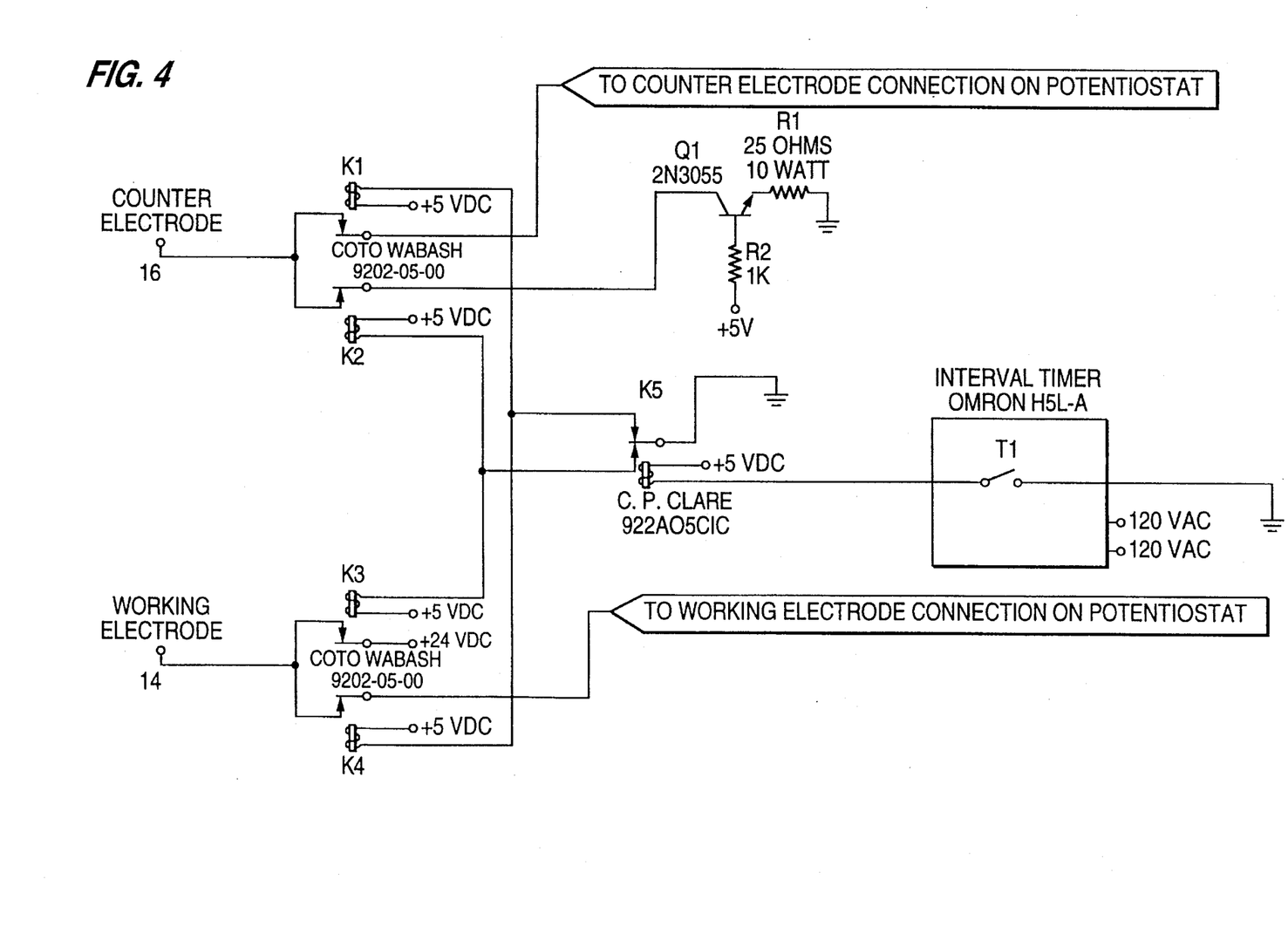
FIG. 4 is a circuit diagram of an electrode cleaning circuit constructed in accordance with a third embodiment of the invention.

In a third embodiment of the invention, metallic or carbon working electrodes in the circuit of the first and second embodiments may be cleaned in situ by electrolysis. An example of a circuit that may be used for cleaning these electrode is shown in FIG. 4. In this circuit, a timer T1 switches the measurement electrodes between the measurement circuit and the cleaning circuit, which will force approximately 150 milliamperes through the working and counter electrodes during the cleaning period. The working electrode is connected to terminal 14 as the anode, and the oxidation of water to produce bubbles of oxygen will boil deposits off the surface of it, thus effectively cleaning the surface.

The circuit shown in FIG. 4 is used to switch the working electrode and the counter electrode (connected at terminal 16) of a voltammetric cell between the measurement circuit and a constant-current source that will electrolyze the water at the surface of the electrodes. The relays used to switch the electrodes must have extremely high insulation resistance ($10^{11}$–$10^{12}$ ohms or greater) to prevent stray leakage current from the constant-current supply from entering the measurement circuit and causing errors. Relays K1 and K4 connect the counter and working electrodes, respectively, to the measurement circuit when relay K5 is de-energized, and relays K2 and K3 connect the counter and working electrodes, respectively, to the constant-current source for cleaning when relay K5 is energized. The coil of relay K5 is energized during the cleaning period by timer T1, such as Omron H5L-A, which is an interval timer that features both variable duty cycle and cycle time. Transistor Q1 and resistors R1 and R2 form the constant current source that can force several hundred milliamperes through the electrodes to produce the desired cleaning action.

Figure 5:
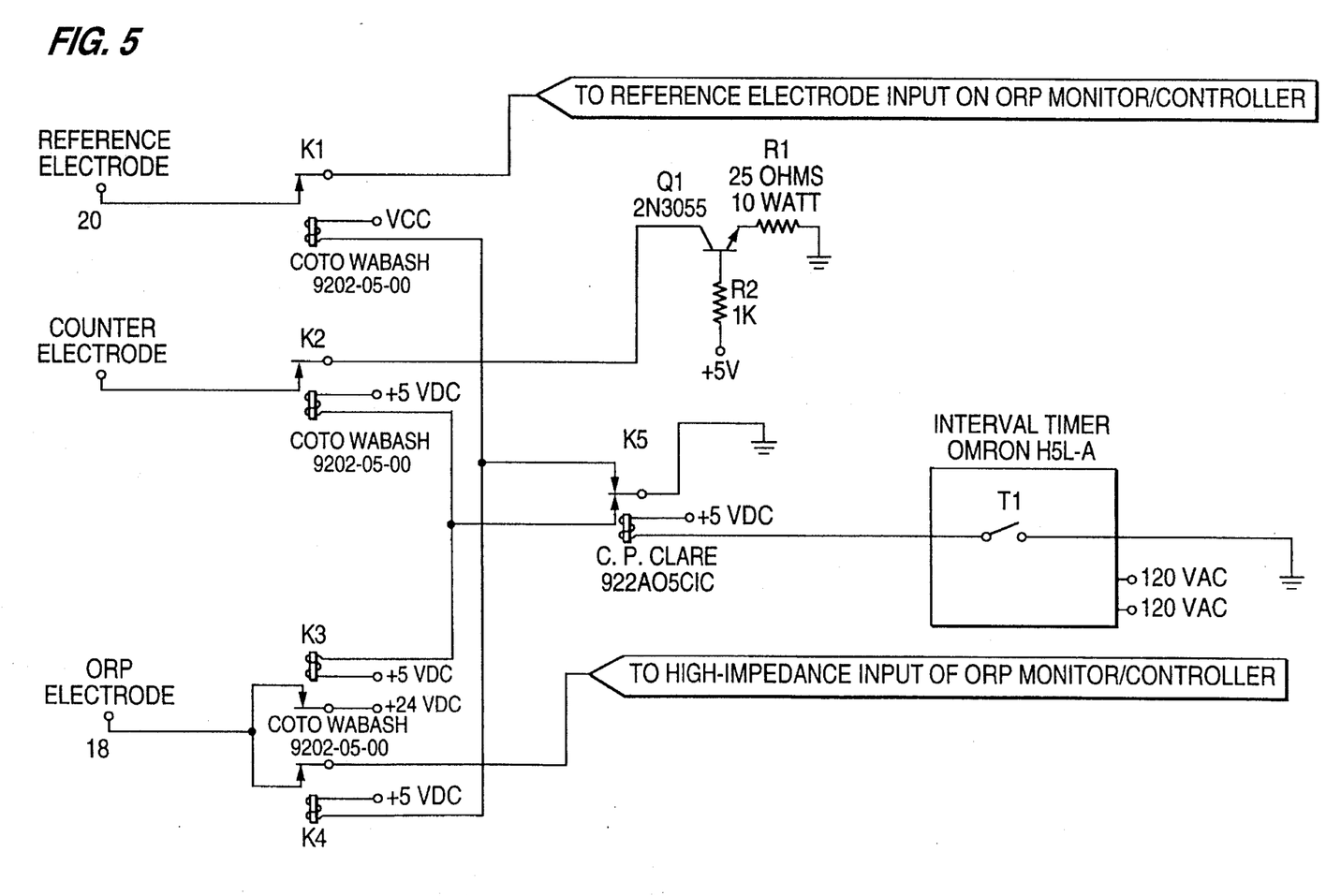
FIG. 5 is a circuit diagram of an oxidation-reduction electrode cleaning circuit constructed in accordance with a fourth embodiment of the invention.

In a fourth embodiment of the invention, a similar circuit is provided to clean electrodes that are used for oxidation-reduction (ORP) measurements as well. An example of this circuit is shown in FIG. 5. In this application, relays K1–K4 used to switch the electrodes between the measurement and cleaning circuits must have very high insulation resistance ($10^{12}$ ohms minimum). Relays of this type are available from Coto Wabash, Inc. of Providence, R.I. Since the reference electrode is grounded in many ORP monitors and controllers, it is important to use a relay to disconnect the reference electrode during the cleaning period in order to prevent damaging current flow through it.

The circuit shown in FIG. 5 is used to switch an oxidation-reduction potential (ORP) electrode (connected at terminal 18) and a reference electrode (connected at terminal 20) in a potentiometric cell between the high-impedance measurement circuit and a constant-current source that will electrolyze the water at the surface of the electrodes. The relays K1–K4 used to switch the electrodes must have extremely high insulation resistance ($10^{11}$–$10^{12}$ ohms or greater) to prevent stray leakage current from the constant-current supply from entering the measurement circuit and causing errors. Likewise, the electrode signal paths should not reside on the surface of the printed circuit board but should be wired point-to-point between contacts mounted on PTFE standoffs. Relays K1 and K4 connect the reference and ORP electrodes, respectively, to the measurement circuit when relay K5 is de-energized, and relays K2 and K3 connect the counter and ORP electrodes, respectively, to the constant-current source for cleaning when relay K5 is energized. The coil of relay K5 is energized during the cleaning period by timer T1, which is an interval timer that features both variable duty cycle and cycle time. Transistor Q1 and resistors R1 and R2 form the constant current source that can force several hundred milliamperes through the electrodes to produce the desired cleaning action.

Figure 6:
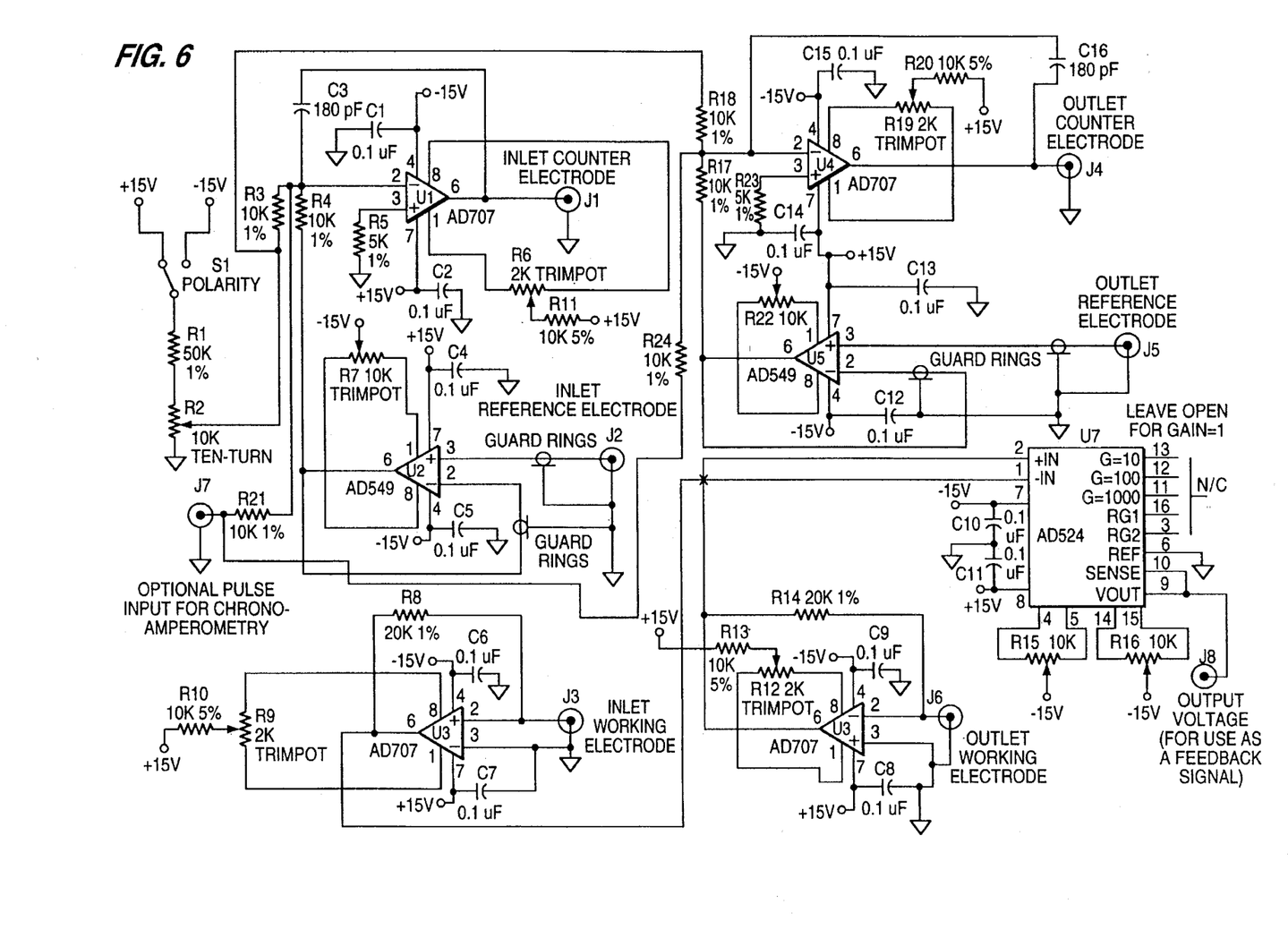
FIG. 6 is a circuit diagram of a differential DC potentiostat constructed in accordance with a fifth embodiment of the invention.

While it is often possible to minimize interferences in voltammetric measurements by adjusting the applied voltage so that interfering substances are not oxidized or reduced, background interferences may be further reduced by measuring the background signal before the water treatment chemical is introduced and subtracting this background signal from the signal that is obtained after the treatment chemical has been added. In continuous flow systems, the background signal is obtained from a set of voltammetric electrodes at the inlet to the treatment tank, and a second set of electrodes at the outlet of the tank can be used to measure the total signal, due to background and added treatment chemical. The difference between these signals is directly proportional to the level of the desired treatment chemical, and this difference signal can be used as a feedback signal for controlling the rate at which the treatment chemical is added. The difference signal is obtained using a differential instrumentation amplifier, such as AD524, manufactured by Analog Devices, Inc. of Norwood, Mass. An example of a circuit that can be used to generate a background-corrected voltammetric measurement, which can be used as a feedback signal for a controller, is shown in FIG. 6. In this circuit, there are two three-electrode potentiostats, one for the inlet of the treatment tank and one for the outlet, and the outputs of current-to-voltage converters in these potentiostats are fed to a differential instrumentation amplifier, from which the output, in turn, is used as a feedback signal. In many instances, this feedback signal must be converted to a 4–20 milliampere signal in order to be transmitted to the controller, and this conversion may be carried out using the AD694 integrated circuit, Analog Devices. This circuit may be modified for use in chronoamperometric measurements by adding (1) a train of applied voltage pulses at terminal J7, which are applied to the inlet cell via R21 and to the outlet cell via R24 and (2) sample-and-hold circuits between the outputs of the current-to-voltage converters (pins 6 of amplifiers U3 and U6) and the + and − inputs of the instrumentation amplifier (pins 1 and 2 of amplifier U7). These sample-and-hold circuits may be implemented using AD7569 integrated circuits from Analog Devices. The read/hold control signal for the sample-and-hold circuits is synchronized with the applied voltage pulse train. The duty cycle of the applied voltage pulse train is kept low enough to allow the solution at the surface of the electrodes to reequilibrate between voltage pulses.

The circuit shown in FIG. 6 is used to determine the difference between the voltammetric signals that are measured in a process or waste stream before a treatment chemical has been added and after it has been added. The difference in the measurement signals will be due solely to the presence of the treatment chemical, and signals due to interfering substances that are present in the stream before the treatment chemical is added will be ignored.

For the voltammetric cell on the inlet or upstream side of the point at which the treatment chemical is added, the potential difference between the reference electrode connected at terminal J2 and working electrode connected at terminal J3, buffered through the high-impedance voltage follower U2, is compared with the desired applied voltage, and the voltage that is applied to the counter electrode connected at terminal J1 is adjusted so that the desired applied voltage appears between the working electrode at terminal J3 and the reference electrode at terminal J2. The potential of the working electrode and the reference electrode is subtracted from the desired applied voltage by adding the desired applied voltage, supplied through R3, to the potential of the reference electrode at terminal J2, which is measured with respect to the working electrode maintained at ground potential and is supplied through resistor R4. This difference signal at the inverting input of amplifier U1 is compared with the potential at the noninverting input of amplifier U1, which is tied to ground through R5, and the resulting error signal is amplified by the open-loop gain of amplifier U1 to supply the appropriate voltage to the counter electrode at terminal J1. The magnitude of the desired applied voltage is determined by the voltage divider R1 and R2, and the polarity is selected by switch S1. Capacitor C3 is needed to prevent oscillation of operational amplifier U1, since this amplifier is used without a feedback loop.

For the voltammetric cell on the outlet or downstream side of the point at which the treatment chemical is added, the potential difference between the reference electrode at terminal J5 and working electrode at terminal J6, buffered through the high-impedance voltage follower U5, is compared with the desired applied voltage, and the voltage that is applied to the counter electrode at terminal J4 is adjusted so that the desired applied voltage appears between the working electrode at terminal J6 and the reference electrode at terminal J5. The potential of working electrode and the reference electrode is subtracted from the desired applied voltage by adding the desired applied voltage, supplied through R18, to the potential of the reference electrode at terminal J5, which is measured with respect to the working electrode at terminal J6, maintained at ground potential, and is supplied through resistor R17. This difference signal at the inverting input of amplifier U4 is compared with the potential at the noninverting input, which is tied to ground through R23, and the resulting error signal is amplified by the open-loop gain of amplifier U4 to supply the appropriate voltage to the counter electrode at terminal J4. Capacitor C16 is needed to prevent oscillation of operational amplifier U4, since this amplifier is used without a feedback loop.

The difference between the output signals from the current-to-voltage converters for the input and output voltammetric cells (amplifiers U3 and U6, respectively) is determined by unity-gain instrumentation amplifier U7, and the output voltage from this amplifier at terminal J8 may be used as a feedback signal for a controller.

Trimpots R6, R7, and R9 are used to null the input offset voltages for amplifiers U1, U2, and U3, respectively, and trimpots R19, R22, and R12 are used to null the input offset voltages for amplifiers U4, U5, and U6, respectively. Resistors R10 and R11 limit current flow through the input offset adjustment circuits for amplifiers U3 and U1, respectively. Resistors R13 and R20 limit current flow through the input offset adjustment circuits for amplifiers U6 and U4, respectively. Trimpots R15 and R16 are used to null the offset voltages for the instrumentation amplifier U7. Capacitors C1–C2 and C4–C15 are used to prevent power supply noise and oscillation.

It will be apparent to those skilled in the art that various modifications and variations can be made in the present invention without departing from the spirit or scope of the invention. Thus, it is intended that the present invention cover the modification and variations of this invention provided they come within the scope of the appended claims and their equivalents.

What is claimed is:

1. A method for controlling the chemical treatment of a solution comprising the steps of:
   (a) feeding a treatment chemical into the solution to obtain a mixture of the treatment chemical and the solution;
   (b) applying an external voltage across a reference electrode and a working electrode of a voltammetric sensor while the electrodes are immersed in and contact the mixture;
   (c) measuring a current that flows through the working electrode;
   (d) converting the measured current into a feedback signal which is indicative of a concentration of a substance in the mixture; and
   (e) using the feedback signal to control a rate of feeding the treatment chemical in step (a).

2. The method according to claim 1, wherein using the feedback signal in step (e) comprises comparing the feedback signal and a reference signal to generate a control signal for controlling the rate of feeding the treatment chemical in step (a).

3. The method according to claim 1, wherein applying an external voltage step (b) comprises applying a d.c. voltage.

4. The method according to claim 1, wherein applying an external voltage step (b) comprises applying a voltage pulse train.

5. The method according to claim 4, wherein measuring a current in step (c) comprises measuring the current after the application of a voltage pulse of the pulse train to permit non-faradaic charging.

6. The method according to claim 1, further comprising the step of:
(f) applying a current to the working electrode sufficient to remove deposits from the working electrode.

7. The method according to claim 1, further comprising the steps of:
measuring a background signal before the treatment chemical is introduced into the solution; and
subtracting the background signal from the feedback signal after the treatment chemical has been introduced into the solution.

8. An apparatus for controlling the amount of treatment chemicals to be added to a solution, comprising:
means for feeding a treatment chemical into the solution to obtain a mixture of the treatment chemical and the solution;
a voltammetric sensor including:
a reference electrode,
a working electrode,
means for applying a voltage across the reference electrode and working electrode while the electrodes are immersed in and contact the mixture,
means for measuring a current that flows through the working electrode, and
means for converting the measured current into a feedback signal which is indicative of a concentration of a substance in the mixture; and
means for applying the feedback signal to the feeding means so as to control a rate of feeding the treatment chemical.

9. The apparatus according to claim 8, further comprising means for comparing the feedback signal with a reference signal to generate a control signal to the feeding means for controlling the rate of feeding the treatment chemical into the solution.

10. The apparatus according to claim 8, further comprising: means for applying a current to the working electrode sufficient to remove deposits from the working electrode.

11. The apparatus according to claim 8, further comprising:
means for measuring a background signal before the treatment chemical is introduced into the solution; and
means for subtracting the background signal from the feedback signal after the treatment chemical has been introduced into the solution.

12. A method for controlling the chemical treatment of a solution comprising the steps of:
(a) feeding a treatment chemical into the solution to obtain a mixture of the treatment chemical and the solution;
(b) applying an external voltage across a counter electrode and a working electrode of a voltammetric sensor while the electrodes are immersed in and contact the mixture;
(c) maintaining a voltage between a reference electrode of the voltammetric sensor and the working electrode at a desired voltage level;

(d) measuring a current that flows through the working electrode;
(e) converting the measured current into a feedback signal which is indicative of a concentration of a substance in the mixture; and
(f) using the feedback signal to control a rate of feeding the treatment chemical in step (a).

13. The method according to claim 12, wherein applying an external voltage step (b) comprises applying a d.c. voltage.

14. The method according to claim 12, wherein applying an external voltage step (b) comprises applying a voltage pulse train.

15. The method according to claim 14, wherein measuring a current in step (b) comprises measuring the current after the application of a voltage pulse of the pulse train to permit a non-faradaic charging current to decay.

16. The method according to claim 12, further comprising the step of:
(g) applying a current to the working electrode sufficient to remove deposits from the working electrode.

17. The method according to claim 12, further comprising the steps of:
measuring a background signal before the treatment chemical is introduced into the solution; and
subtracting the background signal from the feedback signal after the treatment chemical has been introduced into the solution.

18. An apparatus for producing a feedback signal in a system for controlling the amount of treatment chemicals to be added to a solution, comprising:
means for feeding treatment chemicals into the solution to obtain a mixture of the treatment chemicals and the solution;
a voltammetric sensor including:
a reference electrode,
a working electrode,
a counter electrode,
means for applying an external voltage across the counter electrode and working electrode while the electrodes are immersed in and contact the mixture,
means for maintaining a voltage between the reference electrode and working electrode at a desired voltage,
means for measuring a current that flows through the working electrode, and
means for converting the measured current into a feedback signal which is indicative of the concentration of a substance in the mixture; and
means for using the feedback signal to control a rate of feeding the treatment chemicals in the solution.

19. The apparatus according to claim 18, further comprising means for applying a current to the working electrode sufficient to remove deposits from the working electrode.

20. The apparatus according to claim 18, further comprising:
means for measuring a background signal before the treatment chemicals are introduced into the solution; and
means for subtracting the background signal from the feedback signal after the treatment chemical have been introduced into the solution.

* * * * *

UNITED STATES PATENT AND TRADEMARK OFFICE
CERTIFICATE OF CORRECTION

PATENT NO. :    5,470,484
DATED       :    November 28, 1995
INVENTOR(S) :   Thomas E. McNeel It is certified that error appears in the above-indentified patent and that said Letters Patent is hereby corrected as shown below:

Claim 20, column 14, line 62, change "chemical" to

--chemicals--.

Signed and Sealed this

Thirteenth Day of February, 1996

Attest:

BRUCE LEHMAN

*Attesting Officer*     *Commissioner of Patents and Trademarks*